United States Patent
Sanborn et al.

(10) Patent No.: US 7,579,490 B2
(45) Date of Patent: Aug. 25, 2009

(54) CONVERSION OF 2,5-(HYDROXYMETHYL)FURALDEHYDE TO INDUSTRIAL DERIVATIVES, PURIFICATION OF THE DERIVATIVES, AND INDUSTRIAL USES THEREFOR

(75) Inventors: Alexandra J. Sanborn, Lincoln, IL (US); Paul D. Bloom, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 210 days.

(21) Appl. No.: 11/274,554

(22) Filed: Nov. 15, 2005

(65) Prior Publication Data

US 2006/0128844 A1    Jun. 15, 2006

Related U.S. Application Data

(62) Division of application No. 11/070,063, filed on Mar. 2, 2005, now Pat. No. 7,393,963.

(60) Provisional application No. 60/635,406, filed on Dec. 10, 2004.

(51) Int. Cl.
C07D 307/02 (2006.01)
(52) U.S. Cl. ................... 549/503; 549/502; 549/505
(58) Field of Classification Search ............. 549/502, 549/503
See application file for complete search history.

(56) References Cited

U.S. PATENT DOCUMENTS

| | | | |
|---|---|---|---|
| 2,738,367 A | 3/1956 | Redimon et al. | |
| 2,813,900 A | 11/1957 | Dunlop et al. | |
| 2,917,520 A | 12/1959 | Cope | |
| 2,929,823 A | 3/1960 | Garber et al. | |
| 3,025,307 A | 3/1962 | Garber et al. | |
| 3,040,062 A | 6/1962 | Hales | |
| 3,055,914 A | 9/1962 | Garber et al. | |
| 3,066,150 A | 11/1962 | Jones et al. | |
| 3,071,599 A | 1/1963 | Hales et al. | |
| 3,079,449 A | 2/1963 | Cope | |
| 3,083,236 A | 3/1963 | Utne et al. | |
| 3,118,912 A | 1/1964 | Smith | |
| 3,201,331 A | 8/1965 | Hunter | |
| 4,339,387 A | 7/1982 | Fléche et al. | |
| 4,400,468 A * | 8/1983 | Faber ............ | 435/142 |
| 4,590,283 A | 5/1986 | Gaset et al. | |
| 4,740,605 A | 4/1988 | Rapp | |
| 4,935,530 A | 6/1990 | Lee | |
| 5,608,105 A | 3/1997 | Fitzpatrick | |
| 6,518,440 B2 | 2/2003 | Lightner | |
| 6,706,900 B2 | 3/2004 | Grushin et al. | |
| 6,762,230 B2 | 7/2004 | Brandenburger et al. | |
| 2003/0055271 A1 | 3/2003 | Grushin et al. | |
| 2003/0130528 A1 | 7/2003 | Grushin et al. | |

FOREIGN PATENT DOCUMENTS

| | | |
|---|---|---|
| DE | 0 360 1281 A1 | 7/1987 |
| DE | 19615878 | 10/1997 |
| EP | 0 466 409 A1 | 1/1992 |
| EP | 0 862 946 A1 | 9/1998 |
| GB | 0838957 A | 6/1960 |
| GB | 0887360 A | 1/1962 |
| GB | 0888568 A | 1/1962 |
| JP | 3101672 | 4/1991 |
| WO | WO 2005/018799 A1 | 3/2005 |

OTHER PUBLICATIONS

Zhang et al. Journal of Material Science Letters 20, 2001, 993-1994.*

Brochure entitled "Catalysts and Applications of the Chemical Specialties Business Unit," Süd-Chemie Inc., pp. 1, 2, 6, 17, 19-21.

Halliday, Gary A., Robert J. Young, and Vladimir V. Grushin. "One-Pot, Two-Step, Practical Catalytic Synthesis of 2,5-Diformylfuran from Fructose." *Organic Letters* 5 (2003), No. 11, 3pp.

Herring, Andrew M., J. Thomas McKinnon, David E. Petrick, Keith W. Gneshin, Jonathan Filley, and Bryan D. McCloskey. "Detection of reactive intermediates during laser pyrolysis of cellulose char by molecular beam mass spectroscopy, implications for the formation of polycyclic aromatic hydrocarbons." *Journal of Analytical and Applied Pyrolysis*. 66 (2003), pp. 165-182.

Lichtenthaler, Frieder W. "Unsaturated O- and N—Heterocycles from Carbohydrate Feedstocks." *Accounts of Chemical Research*. vol. 35. No. 9. 2002, pp. 728-737.

Lewkowski, Jaroslaw. "Synthesis, Chemistry and Applications of 5-Hydroxymethyl-furfural And Its Derivatives." *Department of Organic Chemistry, University of Lodz, Narutowicza 68, 90-136 Lodz, Poland*. pp. 17-54.

(Continued)

*Primary Examiner*—D. Margaret Seaman
*Assistant Examiner*—Nizal S Chandrakumar
(74) *Attorney, Agent, or Firm*—K & L Gates LLP

(57) ABSTRACT

A method of preparing 2,5-bis(hydroxymethyl)tetrahydrofuran comprises heating a reaction mixture comprising 2,5-(hydroxymethyl)furaldehyde, an organic solvent, and a catalyst system comprising nickel and zirconium at a temperature, for a time, and at a pressure sufficient to promote reduction of the 2,5-(hydroxymethyl)furaldehyde to 2,5-bis(hydroxymethyl)tetrahydrofuran to produce a product mixture comprising 2,5-bis(hydroxymethyl)tetrahydrofuran.

25 Claims, 3 Drawing Sheets

OTHER PUBLICATIONS

Kröger, Martin, Ulf Pruße and Klaus-Dieter Vorlop. "A new approach for the production of 2,5-furandicarboxylic acid by in situ oxidation of 5-hydroxymethylfurfural starting from fructose." *Topics in Catalysis* 13 (2000), pp. 237-242.

Spyroudis, Spyros. "Hydroxyquinones: Synthesis and Reactivity." *Molecules* 2000, pp. 1291-1330.

Tyrlik, Stanislaw K., Dorota Szerszeń, Marian Olejnik, and Witold Danikiewicz. "Selective dehydration of glucose to hydroxymethylfurfural and a one-pot synthesis of a 4-acetylbutyrotactone from glucose and trioxane in solutions of aluminum salts." *Carbohydrate Research* 315 (1999), pp. 268-272.

Moreau, Claude, Robert Durand, Delphine Peyron, Jean Duhamel, and Patrick Rivalier. "Selective preparation of furfural from xylose over microporous solid acid catalysts." *Industrial Crops and Products.* 7 (1998), pp. 95-99.

Lichtenthaler, Frieder W. "Towards Improving the utility of ketoses as organic raw materials." *Carbohydrate Research*. 313 (1998), pp. 69-89.

Gandini, Alessandro, and Mohamed Naceur Belgacem. "Furans in Polymer Chemistry" *Prog. Polym. Sci.* vol. 22, 1997, pp. 1203-1379.

Moreau, Claude, Robert Durand, Cécile Pourcheron, and Sylvie Razigade. "Preparation of 5-hydroxymethylfurfural from fructose and precursors over H-form zeolites." *Industrial Crops and Products.* 3 (1994) pp. 85-90.

Lourvanij, Khavinet, and Gregory, L. Rorrer. "Dehydration of glucose to organic acids in microporous pillared clay catalysts." *Applied Catalysis A:General* 109 (1994), pp. 147-165.

A. Fuchs, Ed. "Inulin and Inulin-containing Crops." *Studies in Plant Science* 3 (1993), pp. 149-160.

Vinke, P., and H. van Bekkum. "The Dehydration of Fructose Towards 5-Hydroxymethylfurfural Using Activated Carbon as Adsorbent." *Starch/stärke* 44 (1992) No. 3, pp. 90-96.

Sanda, Komia, Luc Rigal and Antoine Gaset. "Optimisation of the Synthesis of 5-Chloromethyl-2-furancarboxaidehyde from D-Fructose Dehydration and in-situ Chlorination of 5-Hydroxymethyl-2-furancarboxaldehyde." *Journal of Chemical Technology, Biotechnol.* 0268-2575/92, pp. 139-145.

Chen, Ji-Dong, Ben F.M. Kuster, and Kees Van Der Wiele. "Preparation of 5-Hydroxymethylfurfural via Fructose Acetonides in Ethylene Glycol Dimethyl Ether." *Biomass and Bioenergy* vol. 1 No. pp. 217-223.

Antal, Michael Jerry and William S. L. Mok. Geoffrey N. Richards. "Mechanism of formation of 5-(hydroxymethyl)-2-furaldehyde from D-fructose and sucrose." *Carbohydrate Research*. 199 (1990) pp. 91-109.

Musau, Richard M. and Raphael M. Munavu. "The Preparation of 5-Hydroxymethyl-2-Furaldehyde (HMF) from D-Fructose in the Presence of DMSO." *Biomass* 13 (1987), pp. 67-74.

Jow, Jinder, Gregory L. Rorrer and Martin C. Hawley. "Dehydration of D-Fructose to Levulinic Acid over LZY Zeolite Catalyst." *Biomass* 14 (1987) pp. 185-194.

Van Dam, H.E., P.P.G. Kieboom and H. van Bekkum. "The Conversion of Fructose and Glucose in Acidic Media: Formation of Mydroxymethylfurfural." *Starch/stärke* 38 (1986) No. 3, pp. 95-101.

Jogia, Madhu K., Veikila Vakamoce and Rex T. Weavers. "Synthesis of Some Furfural and Syringic Acid Derivatives." *Aust. J. Chem.*, 1985, 38, pp. 1009-1016.

Hamada, Kazuhiko, Hiroshi Yoshihara, Gohfu Suzukamo and Osamu Hiroaki. "The Dehydration of Ketohexoses into 5-Chloromethyl-2-furaldehyde. The Isolation of Diketohexose Dianhydrides." *Bull. Chem. Soc. Jpn.* 57, 1984, pp. 307-308.

Brown, David W., Arthur J. Floyd, Richard G. Kinsman and Yusuf Roshan-Ali. "Dehydration Reactions of Fructose In Non-aqueous Media." *J. Chem. Biotechnol.* 1982, 32, pp. 920-924.

Szmant, H. Harry and Deena D. Chundury. "The Preparation of 5-Hydroxymethylfurfuraldehyde from High Fructose Corn Syrup and Other Carbohydrates." *J. Chem. Tech. Biotechnol.* 1981, 31, pp. 135-145.

Mercadier, Daniel, Luc Rigal, Antoine Gaset and Jean-Pierre Gorrichon. "Synthesis of 5-Hydroxymethyl-2-furancarboxaldehyde Catalysed by Cationic Exchange Resins. Part 2. Analysis and Discussion of the Effect of the Main Parameters of the HMF Output." *J. Chem. Tech. Biotechnol.* 1981, 31, pp. 497-502.

Mercadier, Daniel, Luc Rigal, Antoine Gaset and Jean-Pierre Gorrichon. "Synthesis of 5-Hydroxymethyl-2-furancarboxaldehyde Catalysed by Cationic Exchange Resins. Part 1. Choice of the Catalyst and the Characteristics of the Reaction Medium." *J. Chem. Tech. Biotechmol.* 1981, 31, pp. 489-496.

Mercadier, Daniel, Luc Rigal, Antoine Gaset and Jean-Pierre Gorrichon. "Synthesis of 5-Hydroxymethyl-2-furancarboxaldehyde Catalysed by Cationic Exchange Resins. Part 3. Kiunetic Approach of the D-Fructose Dehydration." *J. Chem. Tech. Biotechmol.* 1981. 31. pp. 503-508.

Rigal, Luc, Antoine Gaset, and Jean-Pierre Gorrichon. "Selective Conversion of D-Fructose to 5-Hydroxymethyl-2-furancarboxaldehyde Using a Water-Solvent-Ion-Exchange Resin Triphasic System." *Ind. Eng. Chem. Prod. Res. Dev*. 20 (1981), No. 4, pp. 719-721.

Chundury, D. and H.H. Szmant. "Preparation of Polymeric Building Blocks from 5-Hydroxymethyl-and 5-Chloromethylfurfuraldehyde." *Ind. Eng. Chem. Prod. Res. Dev.* 20 (1981), No. 1, pp. 158-163.

Rekker, Roelof F. and Hubertus M. De Kort. "The hydrophobic fragmental constant; an extension to a 1000 data point set." *Eur. J. Med. Chem.* Nov.-Dec. 1979-14 No. 6, pp. 479-488.

Kuster, B.F.M. and J. Laurens. "Preparation of 5-Hydroxymethylfurfural." *Die Starke* 29. 1977 No. 5, pp. 172-176.

Kuster, Ben F.M. and Leo M Tebbens. "Analytical Procedures for Studying the Dehydration of D-Fructose." *Carbohydrate Research* 54 (1977), pp. 159-164.

Kuster, B.F.M. and H.J.C. van der Steen. "Preparation of 5-Hydroxymethylfurfural." *Die Starke* 29, No. 3, pp. 99-103.

Kuster, Ben F.M. and Hessel S. van der Baan. "The Influence of the Initial and Catalyst Concentrations on the Dehydration of D-Fructose." *Carbohydrate Research*. 54 (1977), pp. 165-176.

Kuster, Ben F.M. and Herman M.G. Temmink. "The Influence of pH and Weak-Acid Anions on the Dehydration of D-Fructose." *Carbohydrate Research*. 54 (1977), pp. 185-191.

Leo, Albert, Corwin Hansch and David Elkins. Albert Leo. "Partition Coefficients and their Uses." *Chemical Reviews*. vol. 71. No. 6 Dec. 1971. pp. 525-554, 586-603, 604-605, 555-585, 606-616.

Brady, Jr., Robert F. "Cyclic Acetals of Ketoses." *Carbohydrate Research* 15 (1970), pp. 35-40.

Moye, C.J. and R.J. Goldsack. "Reaction of Ketohexoses with Acid In Certain Non-Aqueous Sugar Solvents." *J. Appl. Chem.*, 1966. vol. 16 July, pp. 206-208.

Wolfrom, Melville L. Ed. "Advances in Carbohydrate Chemistry," *Academic Press* New York and London. 1964, pp. 181-218.

Bonner, T.G., E.J. Bourne and M. Ruszkiewicz, "The Iodine-catalysed Conversion of Sucrose into 5-Hydroxymethylfurfuraldehyde." *Journal of The Chemical Society*, Jan. 1960, pp. 787-791.

Cottier, Louis, Gérard Descotes, Jaroslaw Lewkowski, Romuald Skowroński and Estelle Viollet, "Oxidation of 5-Hydroxymethylfurfural and Derivatives to Furanaldehydes with 2,2,6,6-Tetramethylpiperidine Oxide Radical—Co-oxidant Pairs," *J. Heterocyclic Chem.*, vol. 32, 1995, pp. 927-930.

Cope, Arthur C. and Warren N. Baxter, "Aminoalcohols Containing the 8-Oxa-3-azabicyclo[3.2.1]octane Ring System and Their Benzoates", *(journal title unknown—contribution from the Department of Chemistry, Massachusetts Institute of Technology)* 77 (1955), pp. 393-396.

Turner, James H. Paul A. Rebers, Paul L. Barrick, and Robert H. Cotton, "Determination of 5-(Hydroxymethyl)-2-furaldehyde and Related Compounds", *Analytical Chemistry* 26 (1954), No. 5, pp. 898-901.

Timko, Joseph M., Stephen S. Moore, David M. Walba, Philippe C. Hiberty, and Donald J. Cram, "Host-Guest Complexation. 2. Structural Units That Control Association Constants Between Polyethers and *tert*-Butylammonium Salts", *Journal of the American Chemical Society* 99:13 (1977), pp. 4207-4219.

Brochure entitled "Future Perspectives", Süd-Chemie Inc. (2006) 5 pages.

Kuster, B.F.M., "5-Hydroxymethylfurfural (HMF), A Review Focussing on its Manufacture", *Starch/Stärke* 42 (1990), No. 8, pp. 314-321.

Bobbitt, James M. and M. Cecile L. Flores, "Organic Nitrosoium Salts as Oxidants in Organic Chemistry", *Heterocycles* 27 (1988), No. 2, pp. 509-533.

Haworth, W.N., W.G.M. Jones, and L.F. Wiggins, "The Conversion of Sucrose into Furan Compounds. Part II. Some 2:5-Disubstituted Tetrahydrofurans and their Products of Ring Scission", *Journal of the Chemical Society* (1945), pp. 1-4.

Einhorn, Jacques, Cathy Einhorn, Fabien Ratajczak, and Jean-Louis Pierre, "Efficient and Highly Selective Oxidation of Primary Alcohols to Aldehydes by N-Chlorosuccinimide Mediated by Oxoammonium Salts", *J. Org. Chem.* 61 (1996), pp. 7452-7454.

Bobbitt, James M., "Oxoammonium Salts. 6. 4-Acetylamino-2,2,6,6-tetramethylpiperidine-1-oxoammonium Perchlorate: A Stable and Convenient Reagent for the Oxidation of Alcohols. Silica Gel Catalysis", *J. Org. Chem.* 63 (1998), pp. 9367-9374.

Moore, J.A. and J.E. Kelly, "Polyesters Derived from Furan and Tetrahydrofuran Nuclei", *Macromolecules* 11 (1978), No. 3, pp. 568-573.

Meuser, Friedrich, Norbert Gimmler and Jens Oeding, "Systemanalytische Betrachtung der Derivatisierung von Stärke mit einem Kochextruder als Reaktor", *Starch/Stärke* 42 (1990), No. 9, pp. 330-336.

de Nooy, Arjan E.J., Arie C. Besemer, and Herman van Bekkum, "On the Use of Stable Organic Nitroxyl Radicals for the Oxidation of Primary and Secondary Alcohols", *Synthesis* (1996), pp. 1153-1174.

Leo, A., C. Hansch, and D. Elkins, "Partition Coefficients and Their Uses", *Chemical Reviews* 71 (1971), No. 6 pp. 555-605.

"MP-TsO-Tempo", Argonaut Technologies Inc., Technical Note 509, pp. 1-8.

De Luca, Lidia, Giampaolo Giacomelli, Simonetta Masala, and Andrea Porcheddu, "Trichloroisocyanuric/Tempo Oxidation of Alcohols under Mild Conditions: A Close Investigation.", *Journal of Organic Chemistry* 68(12) (2003), pp. 4999-5001 (abstract only).

* cited by examiner

GC spectrum of product produced from hydrogenation of 5-hydroxymethyl furfural T=200°C, P=1500psig $H_2$, Catalysts =10% run in ethanol.

CONVERSION OF 2,5-(HYDROXYMETHYL)FURALDEHYDE TO INDUSTRIAL DERIVATIVES, PURIFICATION OF THE DERIVATIVES, AND INDUSTRIAL USES THEREFOR

CROSS REFERENCE TO RELATED APPLICATIONS

This application claims priority to, and incorporates by reference, U.S. Provisional Application No. 60/635,406, filed Dec. 10, 2004. This application is a division of U.S. application Ser. No. 11/070,063, filed Mar. 2, 2005 now U.S. Pat. No. 7,393,963, which is incorporated by reference herein in its entirety.

FIELD

Improved methods of synthesizing chemical compounds are disclosed herein. Reduction and oxidation reactions forming important polymeric compounds are disclosed. Methods of optimizing the reduction and oxidation reactions, as well as purification and uses of the reaction products also are disclosed.

BACKGROUND 2,5-(Hydroxymethyl)furaldehyde, also known as 2,5-(hydroxymethyl)-furfural (HMF), has many important industrial and commercial applications, largely due to its many functional groups and ability to serve as a precursor in many polymerization reactions. HMF, for example, is a suitable starting source for the formation of various furan monomers required for the preparation of non-petroleum-derived polymeric materials. HMF, as well as other 2,5-disubstituted furanic derivatives, also has great potential for use in the field of intermediate chemicals produced from regrowing (i.e., renewable) resources. Also due to its various functionalities, HMF may be used to produce a wide range of products, including, but not limited to, polymers, solvents, surfactants, pharmaceuticals, and plant protecting agents. The structure of HMF is shown below:

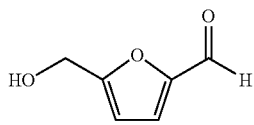

The use of HMF and other furfural derivatives may be compared with the use of corresponding benzene-based macromolecular compounds. In order to be cost-effective and compete in this market, HMF must be produced at competitive prices. The production of HMF has been studied for years, but an efficient and cost-effective method of producing HMF in high yields has yet to be found. HMF is primarily produced from the dehydration reaction of a carbohydrate compound, particularly monosaccharides, including glucose and fructose. After dehydration, complications can arise, such as the rehydratiing of HMF, often yielding the by-products levulinic acid and formic acid. Another competing side reaction is the polymerization of HMF and/or fructose to form humin polymers.

Hexoses are the preferred carbohydrate source from which HMF is formed. Fructose is the preferred hexose used for the dehydration reaction to form HMF. This is in part because fructose has been shown to be more amenable to the dehydration reaction. The fructose structure is shown below:

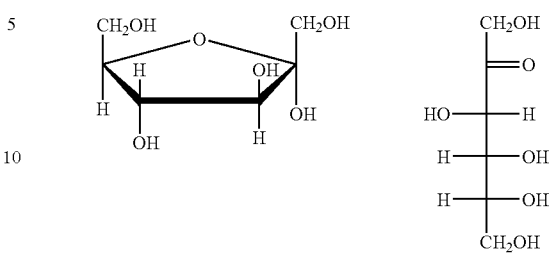

Fructose, however, is more expensive than other hexoses, such as glucose (dextrose), and maltose, for example. Early processes and procedures for the production of HMF focused on the use of crystalline fructose, but its widespread use is prevented by its high cost. Other sources of fructose, including high-fructose corn syrup (HFCS), have been used to produce HMF and other furan derivatives. Szmant and Chundery used high fructose corn syrup as a starting material in forming HMF, as disclosed in a 1981 article in *J. Chem. Tech. Biotechnol.*, 31, (pgs. 135-145). Szmant and Chundry used a variety of carbohydrates as starting material, but designed reaction conditions specific to each carbohydrate source. For example, they used a boron trifluoride catalyst ($BF_3 \cdot Et_2O$) with DMSO as a solvent in the conversion of HFCS to HMF, but utilized different catalyst/solvent combinations with different starting materials. Use of $BF_3 \cdot Et_2O$ as a catalyst is not economically practical since it cannot be recovered and reused. Furthermore, Szmant and Chundry required the use of a Pluronic emulsifier to suppress foaming. They also required bubbling of nitrogen to suppress oxidation and the use of DMSO as a solvent, which is not easily separable from the HMF product, and therefore creates difficulties with product recovery. It remains desirable, therefore, to develop an industrially practicable process for producing HMF in high purit.

U.S. Pat. No. 6,706,900 to Grushin et al. (Grushin '900) also discloses the dehydration of fructose in the form of high-fructose corn syrup, to form HMF as an intermediate; but this process is performed in the context of forming diformylfuran (DFF), also known as 2,5-dicarboxaldehyde. The reaction proceeds in an aqueous environment, and the HMF that is formed is not isolated from the reaction mixture, but rather is directly converted to DFF without an isolation step. The reaction conditions of Grushin '900 are therefore not constrained by considerations of product yields of HMF, as it is formed as an intermediate that is not isolated as a product. More importantly, from a practical commercial standpoint, Grushin '900 is not constrained by considerations of isolating HMF from the product mixture. An efficient method for producing HMF in desirable yields and sufficiently high purity from a natural and industrially convenient carbohydrate source or mixed carbohydrate source has yet to be found.

Water has been used as a solvent of choice in dehydration reactions forming HMF because of the solubility of fructose in water. Aqueous conditions, however, have proven to deleteriously affect the dehydration reaction of fructose to HMF in a variety of ways. Aqueous conditions have led to decreased yield of HMF as low selectivity for the dehydration reaction has been demonstrated. Furthermore, solvation of protons in water highly reduces the catalytic activity for the dehydration reaction. Low selectivity of the dehydration reaction simultaneously leads to increased polymerization reactions and humin formation, which also interfere with the synthesis of HMF.

In an attempt to solve such problems associated with aqueous systems, one proposed solution involves an improvement by simultaneously extracting HMF after the dehydration reaction. A similar attempt to improve yields involves the adsorption of HMF on activated carbon. The key factor in these processes is a rapid removal of HMF from the acidic medium in which it is formed. However, these systems generally suffer from high dilution or partially irreversible adsorption of HMF. These problems have been addressed by a number of different methods, including but not limited to selecting a proper choice of solvents, as disclosed in our co-pending U.S. Provisional Application Ser. No. 60/635,406.

In another attempt to solve the problems of aqueous systems, an organic solvent may be added to the aqueous solution, such as, for example, butanol or dioxane. Such systems, however, present a difficulty in that rehydration of HMF is common and ether formation of HMF occurs with the solvent if alcohols are employed. High yields of HMF, therefore, were not found with the addition of these organic solvents. In a further attempt to provide an adequate solvent system, aqueous solvent mixtures and anhydrous organic solvents have also been employed to ensure favorable reaction conditions. Examples of anhydrous organic solvents used include dimethylformamide, acetonitrile, dimethylsulfoxide, and polyethylene glycol.

Dimethylsulfoxide (DMSO), for example, has been extensively studied and employed as a solvent in the dehydration reaction to form HMF. Improved yields of HMF have been reached with ion exchangers or boron trifluoride etherate as a catalyst, and even without any catalyst. DMSO presents a problem, however, in that recovery of HMF from the solvent is difficult.

Furthermore, although dehydration reactions performed in solvents with high boiling points, such as dimethylsulfoxide and dimethylformamide, have produced improved yields, the use of such solvents is cost-prohibitive, and additionally poses significant health and environmental risks in their use. Still further, purification of the product via distillation has not proven effective for a variety of reasons. First of all, on long exposure to temperatures at which the desired product can be distilled, HMF and impurities associated with the synthetic mixture tend to be unstable and form tarry degradation products. Because of this heat instability, a falling film vacuum must be used. Even in use with such an apparatus however, resinous solids form on the heating surface causing a stalling in the rotor, and the frequent shutdown resulting therefrom makes the operation inefficient.

Catalysts may also be used to promote the dehydration reaction of fructose to HMF. Some commonly used catalysts include cheap inorganic acids, such as $H_2SO_4$, $H_3PO_4$, HCl, and organic acids such as oxalic acid, levulinic acid, and p-toluene sulfonic acid. These acid catalysts are utilized in dissolved form, and as a result pose significant difficulties in their regeneration and reuse, and in their disposal. In order to avoid these problems, solid sulfonic acid catalysts have also been used. Solid acid resins, however, are limited in use by the formation of deactivating humin polymers on their surfaces under conditions taught in the art. Other catalysts, such as boron trifluoride etherate, can also be used. Metals, such as Zn, Al, Cr, Ti, Th, Zr, and V can be used as ions, salts, or complexes as catalysts. Such use has not brought improved results, however, as yields of HMF have continued to be low. Ion exchange catalysts have also been used, but have also delivered low HMF yields under conditions taught in the art, and further limit the reaction temperature to under 130° C., which accordingly limits the yield.

HMF derivatives may be more stable and easier to synthesize than HMF. Derivatives of particular interest include a compound principally derived by the reduction of HMF, 2,5-bis-(hydroxymethyl)tetrahydrofuran (THF-diol), and a compound principally derived by the oxidation of HMF, 2,5-furandialdehyde (2,5-FDA). Because an economically feasible way to produce HMF had not been discovered (prior to the discovery disclosed in U.S. Provisional Application No. 60/635,406), there also been a corresponding lack of interest in the production of these HMF derivatives. The difficulties associated with synthesizing HMF increase the cost of obtaining HMF, and there has been a corresponding lack of the starting material to synthesize THF-diol and 2,5-FDA. Improved methods of synthesizing HMF can be found in our commonly-owned co-pending U.S. Provisional Patent Application Ser. No. 60/635,406, filed Dec. 10, 2004. The structures of HMF and the corresponding derivatives are shown below:

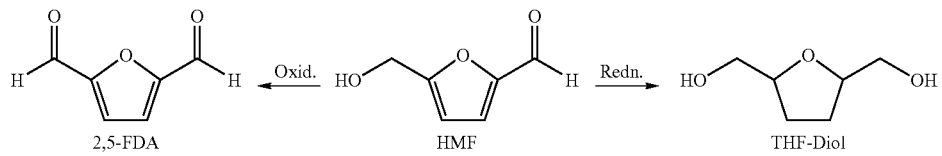

THF-diol is known to be used as a solvent, softener, humectant, and in the synthesis of plasticizers, resins, surfactants, and agricultural chemicals. THF-diol is also known to be used in pharmaceutical applications. THF-diol is typically prepared by Raney nickel reduction of HMF or dimethyl furan-2,5-dicarboxylate. These procedures, however, have not produced suitable yields, and are performed under extreme reaction conditions, both of which make the synthesis unattractive industrially. The reduction of HMF over Raney nickel, for example, is performed at 75 atmospheres and at 130° C. and has not provided satisfactory product yields. Furthermore, because HMF is difficult to obtain commercially, the synthesis of THF-diol from HMF had not been considered a viable industrial alternative. Still further, viable methods of purifying THF-diol have also not been reported, which further has discouraged the search for an efficient synthetic route for making THF-diol.

U.S. Pat. No. 3,083,236 to Utne et al. for example (Utne '236) discloses the synthesis of a number of derivatives from HMF, including THF-glycol. THF glycol is produced mainly as a by-product of other derivatives when using copper chromite as a catalyst under high pressure (approximately 5,000 psi), and Utne '236 also discloses the use of a Raney nickel catalyst, or palladium on charcoal without copper chromite to produce THF-glycol. The reaction conditions, however, require a substantial time period to promote the synthesis.

The synthesis of 2,5-furandialdehyde from HMF has also been attempted, but its industrial application has been limited due to extended reaction times necessary to promote the reaction, harsh reaction conditions (high temperatures), and poor yields, as well as the lack of an industrially acceptable method of synthesizing HMF.

The oxidation of HMF using vanadium catalysts and complex procedures involving bubbling air through the reaction mixture for 24 hours using dimethyl sulfoxide (DMSO) has been thought to be necessary to synthesize 2,5-furandialdehyde. Furthermore, recovery and purification methods for the 2,5-furandialdehyde have been severely limited so that the synthesis has not heretofore been effectively implemented industrially. In sum, economically feasible reactions have not yet been found to synthesize the HMF derivatives THF-diol or 2,5-FDA. Accordingly, a need remains for such reactions.

HMF derivatives have many known uses. In addition, a novel use for such derivatives disclosed herein is as an ingredient of a coating composition. Typical mixtures of liquid paint coatings, including interior latex paint, are dilute solutions of organic resins with organic or inorganic coloring agents, and additives and extenders dissolved in an organic solvent. The organic solvent gives the coating solution the necessary viscosity, surface tension, and other properties necessary to allow application of a smooth layer of the solution. Typical coating solvents, such as ethylene glycol, have high volatility, and contribute substantially to the coatings' volatile organic contents (VOC). VOC is commonly measured in paints, and high VOC is undesirable, as highly volatile organic solvents contribute to lingering paint smells, and may emit fumes arguably contributing to such maladies as "Sick Building Syndrome," "Danish Painters Syndrome," asthma, allergies, and other chemical sensitivities. Accordingly, there is a need for environmentally friendly paints and other coating compositions having reduced volatile organic content, as well as industrially convenient methods of making ingredients that may be included in coating compositions to reduce VOC of such compositions.

SUMMARY

Provided herein is a method of preparing 2,5-bis(hydroxymethyl)-tetrahydrofuran (THF-diol). The method includes heating a reaction mixture comprising 2,5-(hydroxymethyl)furaldehyde (HMF), a solvent, and a catalyst system comprising nickel and zirconium at a temperature, for a time, and at a pressure sufficient to promote the reduction of HMF to THF-diol, to provide a product mixture comprising THF-diol. The solvent may be an organic solvent.

In one non-limiting embodiment of the foregoing method, greater than 90% of HMF is converted to THF-diol. In another non-limiting embodiment, greater than 95% of HMF is converted to THF-diol. In yet another non-limiting embodiment, greater than 99% of HMF is converted to THF-diol. In another non-limiting embodiment of the method, the method is carried out at a temperature between about 190° C. and about 210° C. In another non-limiting embodiment, the method is carried out at a temperature between about 195° C. and about 205° C. In another non-limiting embodiment, the reaction proceeds at a pressure between about 1450 pounds per square inch (psi), and about 1550 psi, while in a further embodiment, the reaction proceeds at a pressure between about 1475 psi and about 1525 psi. In an embodiment, the reaction takes place in a time of less than about three hours. In another embodiment, the reaction takes place in a time of less than about two hours, and in a further embodiment, the reaction takes place in a time of about one hour.

In certain embodiments of the foregoing method, the reduction of HMF to THF-diol takes place while HMF is in solution in an organic solvent selected from the group consisting of ethyl acetate, ethanol, tetrahydrofuran, allyl acetate, methyl propionate, methyl isobutyl ketone, dimethylsulfoxide, and mixtures thereof. In other embodiments of the foregoing method, the method includes the step of isolating THF-diol from the product mixture by a method selected from, for example, and without limitation, fractional distillation and solvent extraction.

According to another aspect of the present disclosure, a further method of preparing THF-diol from a carbohydrate source is provided. The method includes: i) preparing a first reaction mixture comprising a carbohydrate, a solvent and a catalyst; ii) heating the first reaction mixture to a temperature and for a time sufficient to promote acid-catalyzed dehydration of the carbohydrate to form a product comprising HMF; iii) preparing a second reaction mixture by combining the first product with an organic solvent and a catalyst system comprising nickel and zirconium; and iv) heating said second reaction mixture for a time, at a temperature, and at a pressure sufficient to promote reduction of HMF to THF-diol to produce a second product comprising THF-diol. The carbohydrate may be any carbohydrate, such as, but not limited to fructose. The carbohydrate source may be, but is not limited to, high fructose corn syrup (HFCS).

According to yet another aspect of the present disclosure, a method is provided for purifying THF-diol from a composition comprising THF-diol and at least one other material. The method comprises distilling the composition to isolate THF-diol.

According to a further aspect of the present disclosure, a method is provided for purifying THF-diol from a composition comprising THF-diol and at least one other material. The method comprises performing a solvent extraction on the composition.

In another aspect of the present disclosure, a method of preparing 2,5-furandialdehye is disclosed. The method includes: i) reacting in a reaction mixture a material comprising 2,5(hydroxymethyl)furaldehyde; 2,2,6,6-tetramethyl-1-piperidinyloxyl; and an organic oxidant under reaction conditions sufficient to convert 2,5(hydroxymethyl)furaldehyde to 2,5-furandialdehyde, thereby producing a product comprising 2,5-furandialdehyde; and ii) isolating 2,5-furandialdehyde from said product.

In yet a further aspect of the present disclosure, a method of preparing 2,5-furandialdehyde (2,5-FDA) is disclosed. The method includes: i) reacting in a reaction mixture a material comprising HMF with 2,2,6,6-tetramethyl-1-piperidinyloxyl and an organic oxidant in an organic solvent under reaction conditions sufficient to convert HMF to 2,5-FDA to provide a product mixture comprising 2,5-FDA; and ii) isolating 2,5-FDA from the product mixture. The material comprising HMF may be a crude or purified mixture of HMF.

According to yet another aspect of the present disclosure, a coating composition having reduced volatile organic content (VOC) is provided. The coating composition includes a latex polymer comprising a pigment; a coalescent; and THF-diol.

According to a further aspect of the present disclosure, a method of reducing the volatile organic content of a latex paint is provided. The method comprises including THF-diol in the latex paint composition.

DETAILED DESCRIPTION OF CERTAIN EMBODIMENTS

Figure 1:
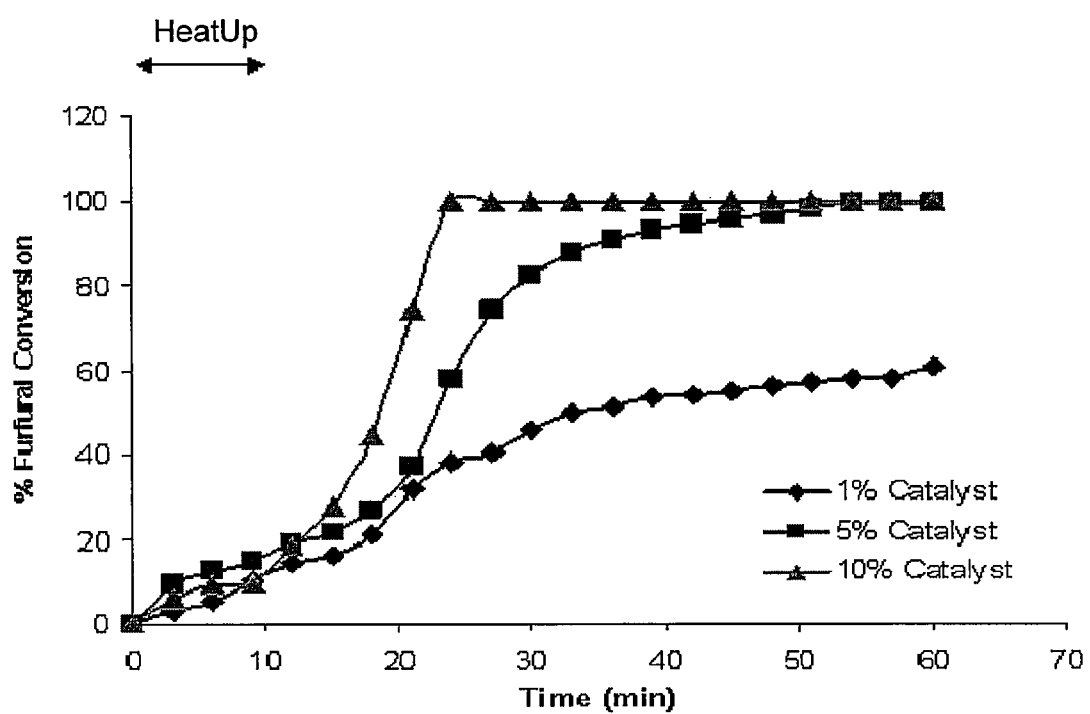
FIG. 1 is a graphic illustration of the effect of the reaction conditions, particularly the catalyst, by monitoring the loss of carbonyl signal and loss of aromaticity.

In a non-limiting embodiment, the reaction of HMF to 2,5-FDA proceeds via an oxidation reaction. The reaction is run with a catalyst and an organic oxidant, and may be performed with or without an organic solvent. In another non-limiting embodiment, the catalyst is 2,2,6,6-tetramethyl-1-piperidinyloxyl (TEMPO). In a certain embodiment, the catalyst is the polymer-bound oxidizing agent (Macroporous polystyrene-bound equivalent of Oxoammonium-p-toluene-sulfonate TEMPO, MP-TSO-TEMPO). In another non-limiting embodiment, the organic oxidant is [bis(acetoxy)-iodo]benzene (BAIB). In a non-limiting embodiment, the organic solvent is selected from the group consisting of methylisobutylketone (MIBK), tetrahydrofuran, ethyl acetate, dichloromethane, dimethylsulfoxide, and combinations thereof.

In another non-limiting embodiment, the oxidation reaction takes place without addition of heat to the reaction. The reaction takes place at room temperature, which is approximately twenty-two degrees Celsius (22° C.). In another non-limiting embodiment, the oxidation reaction takes place under reaction conditions including agitation of the reaction mixture. Agitation of the reaction mixture includes stirring or otherwise mixing the reaction mixture. In one non-limiting embodiment, the reaction mixture is stirred for a time period of about one hour. In a further non-limiting embodiment, the reaction mixture may be stirred for more than an hour. In yet another non-limiting embodiment, 2,5-FDA is isolated from the resulting product mixture by one or more processes selected from the group consisting of distillation, precipitation, solvent extraction, and recrystallization. In another embodiment, 2,5-FDA may be isolated or purified by an adsorptive separation process. An adsorptive separation process may be followed by a desorptive process to separate the target (2,5-FDA) from the adsorptive material. Adsorptive materials are well known in the art, and may be selected from one of the following, such as without limitation, carbon, activated carbon, alumina, and clay. Chromatographic separation processes, such as without limitation, high performance liquid chromatography (HPLC) may also be used. In an embodiment, the molar product yield of 2,5-FDA from HMF is greater than 80%. In a further embodiment, the product yield of 2,5-FDA from HMF is greater than 85%. In still a further embodiment, the product yield of 2,5-FDA from HMF is greater than 95%.

A coating composition also is provided. The coating composition includes THF-diol, a latex polymer comprising a pigment, and a coalescent. The coalescent can be, for example, 2,2,4-trimethyl-1,3-pentanediol monoisobutyrate propionic acid, which is available under the trade name TEXANOL®. In another embodiment the coalescent can be a composition comprising a propylene glycol monoester of one or more vegetable oil fatty acids. An example of such a coalescent is available under the trade name ARCHER RC®. The coating composition including THF-diol has a reduced volatile organic content (VOC). In one non-limiting embodiment, the VOC of the composition is not greater than about 50 grams per liter (g/l), and in another non-limiting embodiment is not greater than 100 g/l. THF-diol can be used as a complete or partial replacement for propylene glycol in coating compositions, and provides a lower VOC content.

As used herein, the "yield" of a reaction refers to the number of moles of product over number of moles of reactant, multiplied by 100 (number of moles of product/number of reactant moles×100).

As used herein, the term, "fractional distillation" refers to a process by which components in a mixture are separated according to their different boiling points. Typically the process entails passing vapors from a boiling solution along a column, wherein the temperature of the column gradually decreases along its length. Components with a higher boiling point condense on the column and return to the solution, and components with a lower boiling point pass through the column and are collected.

As used herein, the term, "solvent extraction" refers to the process of separating components of a mixture by using a solvent which possesses greater affinity for one component, and may therefore separate said one component from at least a second component which is less miscible than said one component with said solvent.

As used herein, the term "crude reaction mixture" refers to a reaction mixture that includes a primary reactant and non-reactant impurities in an industrially convenient conglomerate and that lacks chemical or other refinement. In some instances a crude reaction mixture may be a by-product of another reaction.

As used herein, the term "adsorptive separation process" refers to a method of isolating a target material from a composition comprising at least another material by bringing the composition in flowable contact with an adsorptive material. The adsorptive material has a predetermined greater affinity for the target material compared to the remainder of the composition. The greater affinity provides isolation of the target material from the composition by contact therewith, while the remainder of the composition is not adsorbed by the adsorptive material.

EXAMPLES

Following are examples of reactions forming various derivatives from HMF, methods of purifying and/or isolating the derivatives, and industrial uses for the derivatives. The examples are not meant to limit the scope of the invention, as defined by the claims.

Example 1

PREPARATION OF THF-DIOL FROM HMF REACTION MIXTURE: A reaction mixture containing 54% by weight (wt %) HMF (20.2 g) and anhydrous denatured ethanol (300 ml) was charged into a 1 liter reaction vessel. 3.0 g of G-69B catalyst, obtained from Sud-Chemie, Louisville, Ky., was added to the vessel. (G-69B is a powdered catalyst containing nominally 62% Nickel on Kieselguhr, with a Zirconium promoter, and has an average particle size of 10-14 microns. The manufacturer specifies that it is suitable for hydrogenation of terpene compounds.) The vessel was purged with hydrogen (4×500 pounds per square inch (psi)) with stirring (1000 revolutions per minute (rpm)). The vessel was then pressurized to 1500 psi and heated to 200° C. with continual stirring. After 1 hour, the reaction was allowed to cool to 40° C., and the catalyst removed by vacuum filtration. The solvent was removed by rotary evaporation to provide a brown oil (19.54 g). UV analysis ($\lambda$=284 nm) did not show the presence of HMF, indicating complete conversion of HMF to THF-diol. The complete conversion of HMF to THF-diol was confirmed by GC/MS (m/z=132, 101, 57).

Example 2

PREPARATION OF THF-DIOL FROM HMF: A mixture containing 98% HMF (Aldrich, 5 g) and anhydrous denatured ethanol (300 ml) was placed in a 1 liter reaction vessel. To this mixture was added a heterogenous catalyst 10% G-69B (from Sud-Chemie Inc., Louisville, Ky.), and the reaction was allowed to proceed for 12 hours at 200° C. and 1500 psi. Mass-spectrum: m/z=124 showed that HMF was completely hydrogenated to THF-diol.

Figure 2:
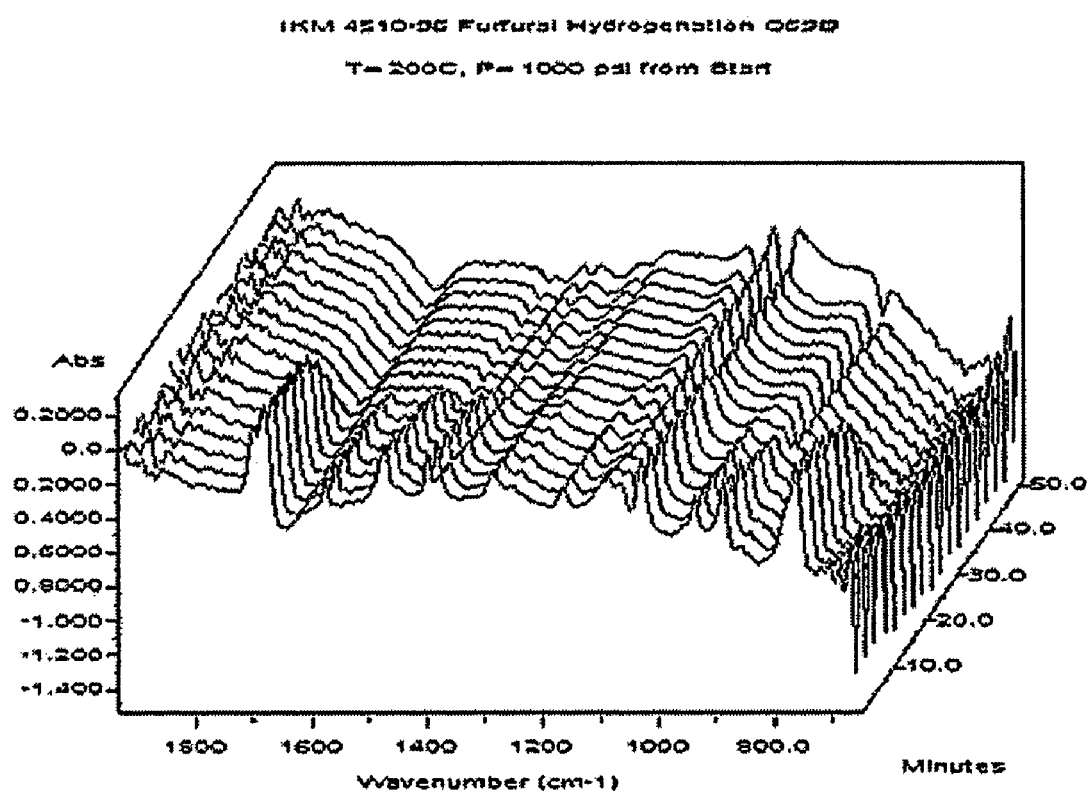
FIG. 2 is a graphic illustration of the effect of the reaction conditions, particularly the catalyst, by monitoring the loss of carbonyl signal and loss of aromaticity.

Experiments were also conducted to determine the most desirable reaction conditions. Some experiments used 2-furaldehyde as a starting material, and hydrogenated the aldehyde group to an alcohol. The reaction was performed under spectroscopic observation, monitoring the loss of the carbonyl group, which represented the point of conversion to the saturated alcohol. 2-furaldehyde was maintained at 200° C. and at 1000 pounds per square inch (psi) hydrogen with varying catalyst loading levels and monitored by infrared spectroscopic analysis (IR). FIGS. 1 and 2 illustrate the effect of the reaction conditions, particularly the catalyst, by monitoring the loss of carbonyl signal and loss of aromaticity.

This experiment shows that higher catalyst loading levels result in rapid conversion. 2-Furaldehyde was used as a readily available compound to show hydrogenation behavior. Then, once the catalyst concentration was worked out, the reaction was run at preferred conditions.

Further IR scans made while the reaction proceeded showed the loss of carbonyl and aromatic ring signals during hydrogenation (FIG. 2). Both furan ring unsaturations and the aldehyde are hydrogenated simultaneously.

Figure 3:
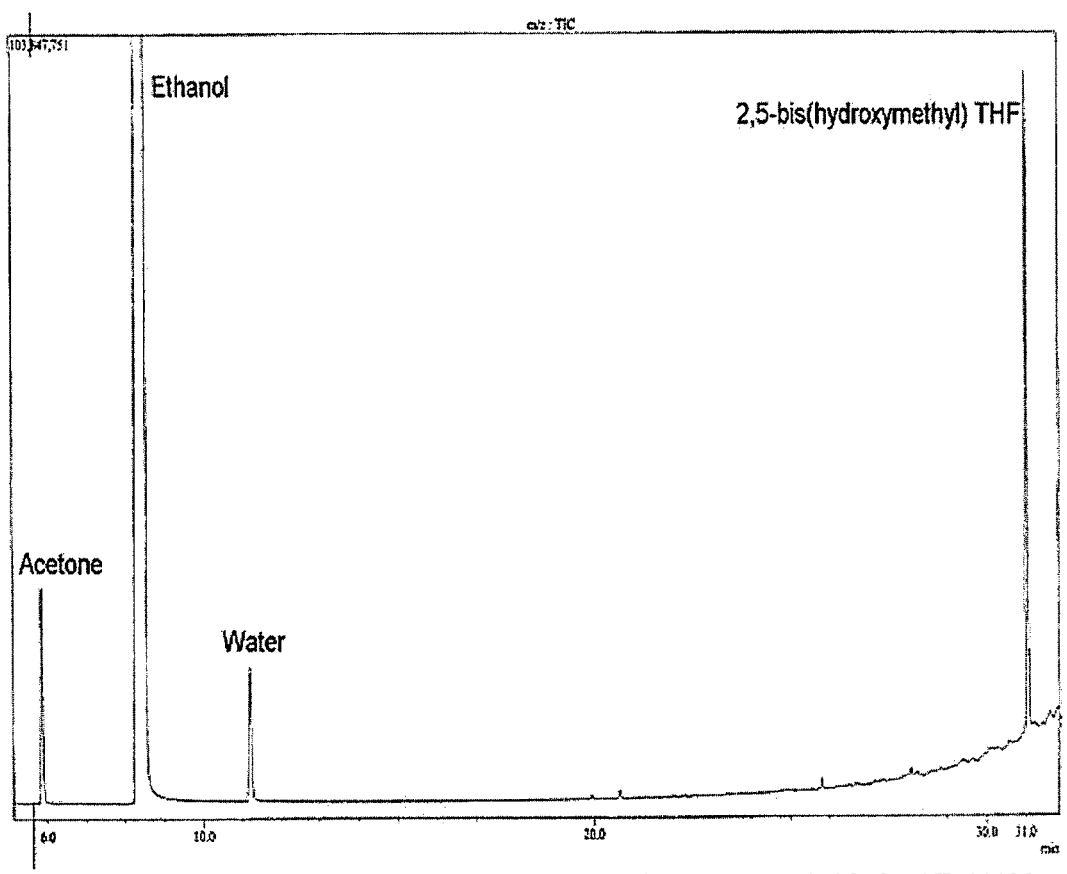
FIG. 3 is a graphic illustration showing experiments involving the conversion of HMF to THF-diol.

FIG. 3 shows experiments involving the conversion of HMF to THF-diol, and confirms the total conversion of HMF to the saturated THF-diol, as there is no signal for the aromatic furan ring or carbonyl aldehyde group after the reaction. The spectrum of FIG. 3 shows that the major product was 2,5-bis(hydroxymethyl) tetrahydrofuran and that the yield of the reaction was essentially quantitative.

Example 3

PREPARATION OF THF-DIOL FROM HMF: An HMF containing distillate (20.8 g, 96% HMF) was placed in ethanol (300 ml), and G-69B catalyst (10%) was added. Hydrogenation was performed at 200° C. and 1500 psi for 1 hour. GC/MS data revealed complete conversion of HMF to THF-diol.

Example 4

PURIFICATION OF THF-DIOL BY FRACTIONAL DISTILLATION: A 18.69 g sample of THF-diol described in above Example 1 was subjected to fractional distillation under reduced pressure (1-2 torr) at 80° C. A bright yellow oil (8.55 g) was isolated. The overall yield of THF-diol from HMF was 76.7%. NMR ($\delta$, 1H): 4.04, (m, 2.0H); 3.94, (b, 4.0H); 3.73, (d, 3.0H); 3.70, (d, 3.0H); 3.59, (m, 3.0H); 3.48, (quartet, 3.0H); 1.88, (m, 1.0H); 1.75, (m, 1.0H).

Example 5

PREPARATION OF PURE THF-DIOL FROM CRUDE HMF REACTION MIXTURE: This example illustrates a method of THF-diol synthesis and purification. In a first step, HMF is purified. A 30.25 g sample of crude HMF material (44% HMF) was added to a mixture of ethyl acetate (45 ml) and water (15 ml). The mixture was stirred at ambient temperature. After 10 minutes, stirring was discontinued and the solution was transferred to a separatory funnel. The two layers were allowed to settle and the organic layer was collected. The aqueous layer was extracted once again with ethyl acetate (30 ml). The organic layers were combined and dried over $MgSO_4$. Following filtration of the $MgSO_4$, the solvent was removed by rotary evaporation to provide 15.19 g of bright red oil of 81.2% pure HMF.

In the second step, THF-diol was synthesized. The sample of purified HMF material (15.19 g) obtained as described in the first step was placed in a 1 liter Parr reactor vessel with ethyl acetate (375 ml) and G-69B catalyst (3.73 g). The vessel was purged 3×500 psi with vigorous stirring (1000 rpm). The pressure was then maintained at 1500 psi with heating to 150° C. for 1 hour. The reaction was allowed to cool and the catalyst removed by filtration. The solvent was removed by rotary evaporation to provide 14.73 g of clear, tan oil. $^1H$ NMR and gc/ms data reveal a high purity THF-diol product (>95%). The overall yield of THF-diol from HMF was 100%. The THF-diol can be decolorized using carbon, as is disclosed in co-pending U.S. Provisional Patent Application No. 60/635,406.

Example 6

SYNTHESIS OF 2,5-FURANDIALDEHYDE (2,5-FDA) FROM PURE HMF USING TEMPO/BAIB: Bisacetoxyiodobenzene catalyst (BAIB, 2.10 g) was added to a solution of HMF (0.76 g) and TEMPO catalyst (83.8 mg) in 10 ml of methyl isobutylketone (MIBK). After 1 hour, TLC analysis indicated that all the alcohol was consumed. The resulting precipitate was filtered and dried. An analytically pure 2,5-FDA sample was obtained (0.20 g); NMR ($\delta$, 1H): 7.40 (s, 2.0H); 9.80 (s, 2.0H); Mass-spectrum: m/z=124. The remaining portion of the reaction was treated with water (5 ml), and the organic layer separated. The aqueous phase was washed with MIBK (20 ml) and the organic layers combined and dried over $MgSO_4$. The drying agent was removed by filtration and the solvent evaporated. The yield of 2,5-FDA from this extraction was 0.38 g. Thus, an overall yield of 80.2% 2,5-FDA was obtained from precipitation and extraction.

Example 7

SYNTHESIS OF 2,5-FDA FROM EXTRACTED HMF USING TEMPO/BAIB: BAIB (2.10 g) was added to a solution of HMF extract (0.89 g, 85% HMF) and TEMPO (94.2 mg) in 15 ml of MIBK. After 1.5 hours stirring at room temperature, TLC analysis indicated all the HMF was consumed. Water (10 ml) was added and the organic layer separated. The aqueous phase was washed with MIBK (20 ml) and the organic layers combined and dried over $MgSO_4$. The drying agent was removed by filtration and the solvent evaporated. The overall yield of 2,5-FDA as an orange powder was 0.65 g (87.3% based on HMF). $^1$H NMR analysis indicates pure 2,5-FDA; NMR (δ, 1H): 7.40 (s, 2.0H); 9.80 (s, 2.0H); Mass-spectrum: m/z=124.

Example 8

PURIFICATION OF 2,5-FDA FROM CRUDE REACTION MIXTURE BY MEANS OF ADSORPTION/DESORPTION: This example illustrates the use of adsorption/desorption as a purifying method for 2,5-FDA from crude reaction mixtures. A sample of crude 2,5-FDA (0.40 g) placed in a mixture of water (40 ml) and NMP (15 ml) was treated with an activated carbon. The activated carbon utilized was Calgon CPG-LF 12×40 carbon (5.0 g). This slurry was allowed to stir at ambient temperature for 48 hours. The carbon was removed by Buchner filtration and collected. GC-MS and TLC analyses of the filtrate indicated completed adsorption of 2,5-FDA onto the carbon. A second water washing (40 ml) of the carbon was performed by stirring overnight at 27° C. The carbon was collected by filtration and placed in ethyl acetate (50 ml). This mixture was allowed to stir at ambient temperature overnight. At this time, TLC analysis indicated the presence of 2,5-FDA in ethyl acetate. The carbon was once again removed by Buchner filtration and washed with ethyl acetate (15 ml). The ethyl acetate was evaporated by rotary evaporation to provide a yellow oil. GC-MS data and $^1$H NMR analysis indicate purified 2,5-FDA (>90%) with residual NMP (<7%).

Example 9

USE OF 2,5-BIS(HYDROXYMETHYL) TETRAHYDROFURAN AS A REPLACEMENT FOR ETHYLENE AND PROPLYENE GLYCOLS IN LATEX PAINTS: 2,5-bis (hydroxymethyl)tetrahydrofuran (THF-diol) was incorporated into interior white latex paint (formula 04-1962-17a; TEXANOL coalescent) as replacement for propylene glycol. The experimental paint formulation is provided in Table 1 below. Various properties of the formulation are reported in Tables 2 and 3 below. The viscosity of the paint containing THF-diol was slightly lower than the viscosity of a control paint made with propylene glycol (see Table 1). The gloss at 20° C. of THF-diol paint was higher than the gloss of control paint, while opacity and CIELab color values were almost identical. Improvements in gloss are advantageous, since lower gloss can be achieved with addition of pigments/flattening agents. In the open-time test, there was little difference between the formulation using THF-diol and control. Sufficient open time is important to maintain a wet edge during paint application. Simply decreasing propylene glycol levels in paint will reduce VOC with simultaneous reduction of open time, if nothing else is added to retard solvent evaporation.

Both THF-diol paint and control paint failed in the freeze-thaw at cycle 1. Propylene glycol and ethylene glycol are known to aid in freeze thaw stability. Equal results indicate that THF-diol has similar function to propylene glycol in this formulation with respect to freeze-thaw stability.

The content of volatiles (wt. %) of THF-diol was 36.14 (EPA Method 24). Replacing propylene glycol in the paint formulation with THF-glycol will help decrease overall VOC. In this example VOC was decreased from 146 g/liter to 97 g/liter. Using both THF-diol and ARCHER RC® coalescent to replace propylene glycol and TEXANOL® coalescent, respectively, would optimize VOC reduction. In the example given, replacement of TEXANOL® coalescent and propylene glycol reduced VOC from 146 g/liter to 64 g/liter. Overall, the amount of VOC reduction will be dependent on the paint formulation. From this evaluation, THF-diol can replace propylene glycol in latex paint formulations to decrease VOC without compromising overall paint performance.

TABLE 1

| Raw Materials | Raw Material Description | Supplier | Lbs. | Gallons |
|---|---|---|---|---|
| Water | | | 17.00 | 2.04 |
| Propylene Glycol or THF-Diol | | Aldrich/ ADM | 26.00 | 3.01 |
| Tamol 1124 | Hydrophilic copolymer pigment dispersant | Rohm and Haas | 1.50 | 0.15 |
| Omyacarb UF | Ultrafine calcium carbonate | OMYA | 52.00 | 2.30 |
| Kathon LX 1.5% | In-can preservative - isothiazolin based | Rohm and Haas | 1.75 | 0.21 |
| TiO2 Slurry 4311 | Titanium dioxide pigment in slurry form | Kronos | 270.00 | 13.85 |
| Water | | | 60.00 | 7.19 |
| Rhoplex SG-30 | 100% acrylic emulsion | Rohm and Haas | 438.00 | 50.95 |
| Polyphase AF-1 | Paint film preservative - IPBC based | Troy Chemical Corp | 12.43 | 1.30 |
| Coalescent | Film former | Eastman Chemical/ADM | 11.22 | 1.42 |
| Aerosol OT-75 | Sodium di-octyl sulfosuccinate Surfactant | Cytec Industries | 1.46 | 0.16 |
| BYK 1660 | Defoamer - emulsion of siloxylated polyether | BYK Chemie | 2.04 | 0.24 |
| Ammonia Water 28% | pH stabilizer | Fisher Scientific | 1.00 | 0.13 |
| Acrysol RM 2020NPR | Hydro-phobically modified oxide urethane (HEUR) rheology modifier | Rohm and Haas | 35.00 | 4.02 |
| Acrysol SCT 275 | Non-ionic polyethylene oxide (HEUR) associative rheology modifier | Rohm and Haas | 14.00 | 1.63 |
| Water | | | 95.12 | 11.39 |
| Total | | | 1038.52 | 100 |

TABLE 2

| Calculate property | Propylene Glycol | THF-dioll | THF-diol Archer RC |
|---|---|---|---|
| Specific Gravity | 1.244 | 1.244 | 1.243 |
| Formula lb/gal | 10.39 | 10.38 | 10.38 |
| % Weight solids | 47.13 | 48.75 | 49.85 |
| VOC less water (g/l) | 146.05 | 97.08 | 64.02 |

TABLE 3

| Properties | White Interior Latex Paint with Propylene Glycol | White Interior Latex Paint with THF-diol |
|---|---|---|
| Viscosity ku/ICI Brookfield KU-1+ Viscometer (ku) ASTM D 562 Brookfield CAP 1000 Viscometer (p) | 98.2/1.488 | 90.7/1.429 |

TABLE 3-continued

| Properties | White Interior Latex Paint with Propylene Glycol | White Interior Latex Paint with THF-diol |
|---|---|---|
| ASTM D 4287 Gloss @ 20°/ 60° ASTM D 523 BYK Gardner Micro-tri-gloss | 13.0/53.7 | 16.5/57.0 |
| Opacity ASTM D 2805 BYK Gardner color-guide 45/0 | 96.37 | 96.45 |
| CIELab ΔE*ab ASTM E 308 BYK Gardner color-guide 45/0 | Std | 0.05 |
| Low Temperature Coalescence (LTC) ASTM D 3793 | Passed | Passed with mapping |
| Freeze-Thaw ASTM D 2243 | Failed at Cycle 1 | Failed at Cycle 1 |
| Heat-aged Stability ASTM D 1849 10 days @ 140° F. | No visible difference on paint quality | |
| Scrub ASTM D 2486 | Equal retention at 1200 cycles | |
| Block ASTM D 4946 | @ RT  @ 120 F. | @ RT  @ 120 F. |
| 1 day curing | 7       5+ | 7−      4-5 |
| 3 days curing | 7+      7− | 7−       6 |
| 7 days curing | 10       9 | 10        9 |

Example 10

SYNTHESIS OF 2,5-FDA FROM PURE HMF USING POLYMER BOUND OXIDIZING AGENT (MP-TsO-TEMPO). This example illustrates the oxidation of HMF using a polymer bound oxidizing agent.

Activation of Oxidizing Agent. To a 10 ml glass vial was added 1.0 g MP-TsO-TEMPO (Agronaut, Foster City, Calif.), dichlorodimethylhydantoin (DCDMH, 0.1 g) and acetonitrile (3 ml). The mixture was shaken manually for 3-4 minutes and the orange solution was removed by pipetting. The resin was washed with acetonitrile (5×5 ml) until the wash was colorless.

Oxidation of HMF. A mixture of freshly activated MP-TsO-TEMPO (1.0 g, 1.0 mmol) and HMF in acetonitrile (3 ml, 0.5 mmol, 0.063 g) was agitated at room temperature. After 4 hours, the solution was removed by pipette and the resin washed with acetonitrile (3×2 ml). The combined solution was concentrated. GC/MS indicated partial conversion to the aldehyde. Mass-spectrum: m/z=124 and m/z=126.

Example 11

SYNTHESIS OF 2,5-FDA FROM PURE HMF USING TEMPO/BAIB AND NEAT REACTION CONDITIONS. This example illustrates the oxidation of HMF using TEMPO/BAIB under neat reaction conditions. To a 20 ml glass vial was added 0.50 g HMF (98% purity, Aldrich), 0.12 g TEMPO, and 1.37 g of BAIB. The solids were mixed well and allowed to sit at room temperature. After only 3 minutes, the reaction mixture became exothermic and liquid and was then chilled to 10° C. To the yellow solid was added hexane and water (8 ml each) and a yellow precipitate was obtained. The precipitate was removed by filtration and dried (0.60 g). $^1$H NMR shows 2,5-FDA of >95% purity. NMR (δ, 1H): 7.40 (s, 2.0H); 9.80 (s, 2.0H).

Example 12

An HMF extract (0.59 g, 85% HMF) as prepared in Example 5, step 1, was treated with TEMPO (0.12 g) and BAIB (1.37 g). The reaction became exothermic and was cooled to 10° C. After 10 minutes, MIBK (2 ml) was added to the mixture and the yellow precipitate was filtered and dried. $^1$H NMR indicates an analytically pure 2,5-FDA (>95% purity).

What is claimed is:

1. A method of preparing 2,5-bis(hydroxymethyl)tetrahydrofuran comprising: heating a reaction mixture comprising 2,5-(hydroxymethyl)furaldehyde, a solvent, and a catalyst system consisting of nominally 62% nickel and a zirconium promoter on a substrate, at a temperature of 150-210° C., a pressure between about 1000 pounds per square inch and about 1550 pounds per square inch, and for a time sufficient to promote reduction of the 2,5-(hydroxymethyl)furaldehyde to 2,5-bis(hydroxymethyl)tetrahydrofuran to produce a product mixture comprising 2,5-bis(hydroxymethyl)tetrahydrofuran.

2. The method of claim 1 wherein greater than 90% of the 2,5-(hydroxymethyl)furaldehyde is converted to 2,5-bis(hydroxymethyl)tetrahydrofuran.

3. The method of claim 1, wherein greater than 95% of the 2,5-(hydroxymethyl)furaldehyde is converted to 2, 5-bis(hydroxymethyl)tetrahydrofuran.

4. The method of claim 3 wherein greater than 99% of the 2,5-(hydroxymethyl)furaldehyde is converted to 2,5-bis(hydroxymethyl)tetrahydrofuran.

5. The method of claim 1 wherein the temperature is between about 195° C. and about 205° C.

6. The method of claim 1 wherein the pressure is between about 1450 pounds per square inch and about 1550 pounds per square inch.

7. The method of claim 6 wherein the pressure is between about 1475 pounds per square inch and about 1525 pounds per square inch.

8. The method of claim 1 wherein the time sufficient to promote reduction of the 2,5-(hydroxymethyl)furaldehyde to 2,5-bis(hydroxymethyl)tetrahydrofuran is less than about three hours.

9. The method of claim 8 wherein the time sufficient to promote reduction of 2,5-(hydroxymethyl)furaldehyde to 2,5-bis(hydroxymethyl)tetrahydrofuran is less than about two hours.

10. The method of claim 9 wherein the time sufficient to promote reduction the 2,5-(hydroxymethyl)furaldehyde to 2,5-bis(hydroxymethyl)tetrahydrofuran is about one hour.

11. The method of claim 1 wherein the solvent is selected from the group consisting of ethyl acetate, ethanol, tetrahydrofuran, methyl propionate, methyl isobutyl ketone, dimethylsulfoxide, and combinations thereof.

12. The method of claim 1 further comprising:
isolating 2,5-bis(hydroxymethyl)tetrahydrofuran from the product mixture by one of fractional distillation and solvent extraction.

13. A method of preparing 2,5-bis(hydroxymethyl)tetrahydrofuran comprising:
heating a reaction mixture comprising 2,5-(hydroxymethyl)furaldehyde, a solvent, and a catalyst system consisting of nominally 62% nickel and a zirconium promoter on a substrate, at a temperature between about 190° C. and about 210° C., for a time less than about three hours, and at a pressure between about 1450 pounds per square inch and about 1550 pounds per square inch to promote reduction of the 2,5-(hydroxymethyl)furaldehyde to 2,5-bis(hydroxymethyl)tetrahydrofuran to produce a product mixture comprising 2,5-bis(hydroxymethyl)tetrahydrofuran.

14. The method of claim 13, wherein greater than 90% of the 2,5-(hydroxymethyl)furaldehyde is converted to 2,5-bis(hydroxymethyl)tetrahydrofuran.

15. The method of claim 13, wherein greater than 95% of the 2,5-(hydroxymethyl)furaldehyde is converted to 2,5-bis(hydroxymethyl)tetrahydrofuran.

16. The method of claim 13, wherein greater than 99% of the 2,5-(hydroxymethyl)furaldehyde is converted to 2,5-bis(hydroxymethyl)tetrahydrofuran.

17. A method of preparing 2,5-bis(hydroxymethyl)tetrahydrofuran comprising: heating a reaction mixture comprising 2,5-(hydroxymethyl)furaldehyde, a solvent, and a catalyst system consisting of nominally 62% nickel and a zirconium promoter on a substrate, at a temperature between about 150° C. and about 210° C., a pressure between about 1000 pounds per square inch and about 1550 pounds per square inch, and for a time sufficient to promote reduction of the 2,5-(hydroxymethyl)furaldehyde to 2,5-bis(hydroxymethyl)tetrahydrofuran to produce a product mixture comprising 2,5-bis(hydroxymethyl)tetrahydrofuran, wherein greater than 90% of the 2,5-(hydroxymethyl)furaldehyde is converted to 2,5-bis(hydroxymethyl)tetrahydrofuran; and isolating 2,5-bis(hydroxymethyl)tetrahydrofuran from the product mixture by one of fractional distillation and solvent extraction.

18. The method of claim 17, wherein the temperature is between about 190° C. and about 210° C.

19. The method of claim 17, wherein the pressure is between about 1450 pounds per square inch and about 1550 pounds per square inch.

20. The method of claim 1, wherein the catalyst system consisting of nickel and zirconium comprises up to a 10% catalyst loading level.

21. The method of claim 1, wherein the catalyst system consisting of nickel and zirconium comprises up to a 5% catalyst loading level.

22. The method of claim 13, wherein the catalyst system consisting of nickel and zirconium comprises up to a 10% catalyst loading level.

23. The method of claim 13, wherein the catalyst system consisting of nickel and zirconium comprises up to a 5% catalyst loading level.

24. The method of claim 17, wherein the catalyst system consisting of nickel and zirconium comprises up to a 10% catalyst loading level.

25. The method of claim 17, wherein the catalyst system consisting of nickel and zirconium comprises up to a 5% catalyst loading level.

* * * * *